(12) United States Patent
Sugimoto

(10) Patent No.: US 9,944,852 B2
(45) Date of Patent: Apr. 17, 2018

(54) HIGH-PURITY 1H-HEPTAFLUOROCYCLOPENTENE

(71) Applicant: ZEON CORPORATION, Tokyo (JP)

(72) Inventor: Tatsuya Sugimoto, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 14/769,264

(22) PCT Filed: Feb. 19, 2014

(86) PCT No.: PCT/JP2014/053863
§ 371 (c)(1),
(2) Date: Aug. 20, 2015

(87) PCT Pub. No.: WO2014/129488
PCT Pub. Date: Aug. 28, 2014

(65) Prior Publication Data
US 2016/0002530 A1  Jan. 7, 2016

(30) Foreign Application Priority Data

Feb. 21, 2013 (JP) .................................. 2013-031599

(51) Int. Cl.
| | |
|---|---|
| B44C 1/22 | (2006.01) |
| C03C 15/00 | (2006.01) |
| C03C 25/68 | (2006.01) |
| C23F 1/00 | (2006.01) |
| H01L 21/302 | (2006.01) |
| H01L 21/461 | (2006.01) |
| C09K 13/00 | (2006.01) |
| H01L 21/02 | (2006.01) |
| C23F 1/12 | (2006.01) |
| C07C 17/23 | (2006.01) |
| C07C 17/383 | (2006.01) |
| C07C 23/08 | (2006.01) |
| H01L 21/3065 | (2006.01) |
| B65D 25/38 | (2006.01) |

(52) U.S. Cl.
CPC .............. *C09K 13/00* (2013.01); *B65D 25/38* (2013.01); *C07C 17/23* (2013.01); *C07C 17/383* (2013.01); *C07C 23/08* (2013.01); *C23F 1/00* (2013.01); *C23F 1/12* (2013.01); *H01L 21/02271* (2013.01); *H01L 21/02274* (2013.01); *H01L 21/3065* (2013.01); *C07C 2601/10* (2017.05); *H01L 21/0262* (2013.01); *H01L 21/02263* (2013.01)

(58) Field of Classification Search
None
See application file for complete search history.

(56) References Cited

U.S. PATENT DOCUMENTS

| | | | |
|---|---|---|---|
| 6,395,700 B1 | 5/2002 | Yamada et al. | |
| 2010/0264116 A1 | 10/2010 | Suzuki et al. | |
| 2011/0060170 A1 * | 3/2011 | Sugimoto | ............... C07C 17/23 570/153 |

FOREIGN PATENT DOCUMENTS

| | | |
|---|---|---|
| EP | 2 194 569 A1 | 6/2010 |
| JP | 11-292807 A | 10/1999 |
| JP | 2000-86548 A | 3/2000 |
| JP | 2009-206444 A | 9/2009 |
| JP | 2010-43034 A | 2/2010 |
| JP | 2010-126452 A | 6/2010 |
| JP | 2011-105625 * | 6/2011 |
| JP | 2011-105625 A | 6/2011 |
| WO | 99/33771 A1 | 7/1999 |
| WO | 2009041560 A1 | 4/2009 |
| WO | 2010/007968 A1 | 1/2010 |

OTHER PUBLICATIONS

Extended (supplementary) European Search Report dated Aug. 17, 2016, issued in counterpart Application No. 14754553.7. (8 pages).
International Search Report dated Apr. 22, 2014, issued in counterpart Application No. PCT/JP2014/053863 (2 pages).
Written Opinion dated Apr. 22, 2014, Issued in counterpart International application No. PCT/JP2014/053863. (5 pages).

* cited by examiner

*Primary Examiner* — Stephanie P Duclair
(74) *Attorney, Agent, or Firm* — Westerman, Hattori, Daniels & Adrian, LLP

(57) ABSTRACT

The present invention is a 1H-Heptafluorocyclopentene having a purity of 99.9 wt % or more and an organochlorine-based compound content of 350 ppm by weight or less. The present invention provides a high-purity 1H-Heptafluorocyclopentene that may be useful as a plasma reaction gas for semiconductors.

7 Claims, No Drawings

HIGH-PURITY 1H-HEPTAFLUOROCYCLOPENTENE

TECHNICAL FIELD

The present invention relates to high-purity 1H-heptafluorocyclopentene that may be useful as a plasma reaction gas (e.g., dry etching gas or CVD gas), a fluorine-containing medicine intermediate, a hydrofluorocarbon-based solvent, and the like.

BACKGROUND ART

In recent years, semiconductor production technology that achieves further miniaturization has been developed, and a line width of 20 nm or 10 nm has been used for a leading-edge process. The processing difficulty level has increased along with miniaturization, and various techniques are currently under development using various approaches (e.g., material, device, and processing method).

In view of the above situation, 1H-heptafluorocyclopentene has been developed as a dry etching gas that can also be used for a leading-edge dry etching process (see Patent Document 1). 1H-Heptafluorocyclopentene exhibits superior performance as compared with hexafluoro-1,3-butadiene (that is widely used on an industrial scale) when used as an etching gas for etching a silicon oxide film, and the utility thereof has attracted attention.

1H-Heptafluorocyclopentene may be produced using a method that hydrogenates octafluorocyclopentene to obtain 1H-2H-octafluorocyclopentane, and brings the resulting 1H,2H-octafluorocyclopentane into contact with a basic compound potassium carbonate) to effect dehydrofluorination (see Patent Document 2), or a method that hydrogenates (chlorine atom hydrogenation) 1-chloroheptafluorocyclopentene in the presence of a palladium-based hydrogenation catalyst (see Patent Document 3), for example.

RELATED-ART DOCUMENT

Patent Document

Patent Document 1: WO2009/041560
Patent Document 2: JP-A-11-297807
Patent Document 3: WO2010/007968

SUMMARY OF THE INVENTION

Technical Problem

As described above, 1H-heptafluorocyclopentene has attracted attention as a dry etching gas that can also be used for a leading-edge dry etching process.

However, when dry etching is performed while continuously feeding 1H-heptafluorocyclopentene to a dry etching device in a state in which a container is filled with 1H-heptafluorocyclopentene, the etching rate may gradually decrease, and etching may stop in some cases.

The inventor of the invention conducted extensive studies in order to solve the above problem. As a result, the inventor found that a decrease in etching rate occurs due to impurities (particularly a trace amount of organochlorine-based compound) included in 1H-heptafluorocyclopentene and also found that the organochlorine-based compound (impurities) is concentrated in the container during dry etching, and the purity of 1H-heptafluorocyclopentene decreases when the amount of 1H-heptafluorocyclopentene contained in the container has decreased, whereby a decrease in etching rate occurs. The inventor found that, when using high-purity 1H-heptafluorocyclopentene provided in a container as a dry etching gas (or a CVD gas), it is necessary to limit the amount of organochlorine-based compound included in 1H-heptafluorocyclopentene to be equal to or less than a given value in order to implement stable dry etching until the container becomes almost empty. This finding has led to the completion of the invention.

Solution to Problem

Several aspects of the invention provide the following 1H-heptafluorocyclopentene (see (1) to (5)), method for using 1H-heptafluorocyclopentene (see (6) and (7)), and container equipped with a valve (see (8)).

(1) 1H-Heptafluorocyclopentene having a purity of 99.9 wt % or more and an organochlorine-based compound content of 350 ppm by weight or less.
(2) The 1H-heptafluorocyclopentene according to (1), the 1H-heptafluorocyclopentene being obtained by performing a step (I) that hydrogenates 1-chloroheptafluorocyclopentene through a gas phase reaction in the presence of a catalyst to obtain crude 1H-heptafluorocyclopentene, and a step (II) that purifies the crude 1H-heptafluorocyclopentene obtained by the step (I) using a rectifying column that has a number of theoretical plates of 50 or more.
(3) The 1H-heptafluorocyclopentene according to (1), wherein the organochlorine-based compound is either or both of chlorononafluorocyclopentane and chloroheptafluorocyclopentene.
(4) The 1H-heptafluorocyclopentene according to (1), the 1H-heptafluorocyclopentene having a nitrogen content of 100 ppm by volume or less and an oxygen content of 50 ppm by volume or less.
(5) The 1H-heptafluorocyclopentene according to (3), the 1H-heptafluorocyclopentene having a water content of 20 ppm by weight or less.
(6) A method for using the 1H-heptafluorocyclopentene according to any one of (1) to (5) as a dry etching gas.
(7) A method for using the 1H-heptafluorocyclopentene according to any one of (1) to (5) as a plasma CVD reactive gas.
(8) A container equipped with a valve that is filled with the 1H-heptafluorocyclopentene according to any one of (1) to (5).

Advantageous Effects of the Invention

The high-purity 1H-heptafluorocyclopentene according to one aspect of the invention may suitably be used as a plasma etching gas, a chemical vapor deposition (CVD) reactive gas, and the like in the field of production of semiconductor devices that utilizes a plasma reaction.

DESCRIPTION OF EMBODIMENTS

1H-Heptafluorocyclopentene according to one embodiment of the invention has a purity of 99.9 wt % or more and an organochlorine-based compound content of 350 ppm by weight or less.

The nitrogen content and the oxygen content in the 1H-heptafluorocyclopentene according to one embodiment of the invention are preferably 100 ppm by volume or less and 50 ppm by volume or less, respectively and the water content in the 1H-heptafluorocyclopentene according to one embodiment of the invention is preferably 20 ppm by weight or less.

Note that the purity of the 1H-heptafluorocyclopentene according to one embodiment of the invention and the organochlorine-based compound content in the 1H-heptafluorocyclopentene according to one embodiment of the invention refer to values determined by gas chromatography using a flame ionization detector (FID).

The organochlorine-based compound may be identified by gas chromatography-mass spectrometry.

The nitrogen content and the oxygen content in the 1H-heptafluorocyclopentene according to one embodiment of the invention refer to values determined by gas chromatography using a thermal conductivity detector (TCD).

The water content in the 1H-heptafluorocyclopentene according to one embodiment of the invention refers to a value determined by FT-IR.

The high-purity 1H-heptafluorocyclopentene according to one embodiment of the invention may be produced using an arbitrary method as long as the 1H-heptafluorocyclopentene has a purity of 99.9 wt % or more and an organochlorine-based compound content of 350 ppm by weight or less.

It is preferable to produce the high-purity 1H-heptafluorocyclopentene according to one embodiment of the invention by performing a step (II) that purifies crude 1H-heptafluorocyclopentene using a rectifying column that has a number of theoretical plates of 50 or more.

Production of Crude 1H-heptafluorocyclopentene

The crude 1H-heptafluorocyclopentene may be produced using the method disclosed in JP-A-11-292807 or WO2010/007968. The method disclosed in JP-A-11-292807 converts octafluorocyclopentene into 1H,2H-octafluorocyclopentane using hydrogen gas in the presence of a hydrogenation catalyst, and subjects the resulting 1H,2H-octafluorocyclopentane to a dehydrofluorination reaction in the presence of an alkali to obtain the desired crude 1H-heptafluorocyclopentene. The method disclosed in WO2010/007968 hydrogenates (via chlorine atom hydrogenation reaction) 1-chloroheptafluorocyclopentene using hydrogen gas in the presence of a hydrogenation catalyst to obtain crude 1H-heptafluorocyclopentene. It is preferable to produce the crude 1H-heptafluorocyclopentene rising the method disclosed in WO2010/007968 from the viewpoint of industrial production taking account of the number of production steps, ease of operation, the raw material cost, and the like.

Purification of Crude 1H-heptafluorocyclopentene

Organic impurities are removed from the crude 1H-heptafluorocyclopentene (obtained by hydrogenating 1-chloroheptafluorocyclopentene) using a distillation purification method or the like. A rectifying column is used when removing organic impurities using a distillation purification method. In particular, it is preferable to use a rectifying column having a large number of theoretical plates in order to efficiently remove organic impurities having a boiling point close to that (46° C.) of 1H-heptafluorocyclopentene. The number of theoretical plates of the rectifying column is normally 30 or more, and preferably 50 or more. The upper limit of the number of theoretical plates is preferably 100 or less from the viewpoint of production efficiency.

The pressure (gauge pressure) applied during rectification is normally set to between normal pressure and 5 atmospheres, and preferably set to between normal pressure and about 2 atmospheres. The ratio of the reflux rate to the distillate rate (hereinafter may be referred to as "reflux ratio") is preferably set to 40:1 or more in order to remove trace amounts of impurities included in 1H-heptafluorocyclopentene (particularly impurities having a boiling point close to that of 1H-heptafluorocyclopentene). If the reflux ratio is too low, it may be difficult to efficiently remove trace amounts of impurities, and sufficiently increase the purity of 1H-heptafluorocyclopentene. Moreover, since the amount of initial distillate may increase, the amount of 1H-heptafluorocyclopentene (collected as a product) may substantially decrease. If the reflux ratio is too high, collection (per distillation) may take time, and the rectification time may increase.

A batchwise rectification method may be used when the production volume is small. When the production volume is large, a continuous rectification method that utilizes several rectifying columns may be used. An extractive distillation operation that utilizes an extraction solvent may be performed in combination with rectification.

The organic impurities include a compound having a boiling point lower than that of 1H-heptafluorocyclopentene, and a compound having a boiling point higher than that of 1H-heptafluorocyclopentene. Distillation purification may be designed so that a compound having a boiling point lower than that of 1H-heptafluorocyclopentene is removed by the first distillation operation, and a compound having a boiling point higher than that of 1H-heptafluorocyclopentene is removed by the second distillation operation (i.e., multistep distillation), for example. In this case, it is also preferable to set the reflux ratio to 40:1 or more.

When purifying the crude 1H-heptafluorocyclopentene using a rectifying column, rectification may be performed in a Group 0 gas (inert gas). The Group 0 gas (inert gas) is not particularly limited. Examples of the Group 0 gas (inert gas) include helium, neon, argon, krypton, xenon, and the like (that belong to Group 0 in the periodic table). Among these, helium and argon are preferable from the viewpoint of industrial availability.

The 1H-heptafluorocyclopentene according to one embodiment of the invention (for which the purity has been increased to 99.9 wt % or more using the above method) includes trace amounts of reaction raw materials and by-products (organic impurities) that may be produced during production of 1H-heptafluorocyclopentene. Specific examples of such organic impurities include octafluorocyclopentene, heptafluorocyclopentanone, chlorononafluorocyclopentane, and 1-chloroheptafluorocyclopentene.

If large amounts of chlorononafluorocyclopentane (that has a boiling point (52° C.) higher than that (46° C.) of 1H-heptafluorocyclopentene) and 1-chloroheptafluorocyclopentene (that has a boiling point (56° C.) higher than that (46° C.) of 1H-heptafluorocyclopentene) are present in 1H-heptafluorocyclopentene, concentration occurs when the amount of 1H-heptafluorocyclopentene contained in a container has decreased when 1H-heptafluorocyclopentene is continuously fed to an etching device in a state in which the container is filled with 1H-heptafluorocyclopentene.

When 1H-heptafluorocyclopentene that includes a concentrate of chlorononafluorocyclopentane and 1-chloroheptafluorocyclopentene (i.e., organochlorine-based compound) is used as a dry etching gas, the etching rate may decrease, or etching may stop halfway. In this case, the apparent amount of 1H-heptafluorocyclopentene contained in the container decreases, and the yield of semiconductor devices decreases.

A problem may occur if the nitrogen content and the oxygen content in 1H-heptafluorocyclopentene are high. If the nitrogen content is high, or varies depending on the container, the etching rate may significantly change (i.e., the etching rate may vary depending on the batch) during thy etching, and the stability of the production process may be impaired. The deposition properties of 1H-heptafluorocyclopentene may change (i.e., the selectivity of the etching target material may decrease or vary) due to oxygen during dry etching (depending on the etching target material and the production process). Therefore, it is preferable that the nitrogen content and the oxygen content in 1H-heptafluorocyclopentene be as low as possible.

Nitrogen and oxygen included in 1H-heptafluorocyclopentene may be removed using an arbitrary method. For example, nitrogen and oxygen included in 1H-heptafluorocyclopentene may be removed by removing the organochlorine-based compound by rectification using a Group 0 gas (inert gas), or subjecting 1H-heptafluorocyclopentene to simple distillation, and removing a fraction. When using the latter method, the nitrogen content and the oxygen content in 1H-heptafluorocyclopentene that remains in a still are reduced by subjecting nitrogen and oxygen to simple distillation together with 1H-heptafluorocyclopentene. The nitrogen content and the oxygen content in 1H-heptafluorocyclopentene that has been subjected to distillation are preferably 20 to 50 wt %, and more preferably 30 to 40 wt %, based on 1H-heptafluorocyclopentene that is put into the still. The resulting 1H-heptafluorocyclopentene may be stored, and added to the net batch (i.e., can be recycled).

Water included in 1H-heptafluorocyclopentene may be removed using an arbitrary method. Water included in 1H-heptafluorocyclopentene may be removed using a normal method such as a method that brings 1H-heptafluorocyclopentene into contact with an adsorbent.

A molecular sieve, alumina, or the like may be used as the adsorbent. A molecular sieve or alumina may be appropriately selected from various commercially-available products. When using a molecular sieve, it is preferable to use a molecular sieve 3A, 4A, 5A, or the like (more preferably a molecular sieve 3A). When using alumina, it is preferable to use activated alumina that has low crystallinity and is produced by subjecting alumina hydrate to thermal dehydration. It is preferable to activate the adsorbent (e.g. molecular sieve or alumina) by calcination or the like before bringing 1H-heptafluorocyclopentene into contact with the adsorbent. The activated adsorbent can adsorb a larger amount of water. The water content in 1H-heptafluorocyclopentene can be reduced to 20 ppm by weight or less by bringing 1H-heptafluorocyclopentene into contact with the adsorbent. If the water content is high, water may adhere to (remain on) the processing target surface of a substrate after etching, and delamination of a laminate film may occur when forming a copper wire or the like, or the embedded wire may be corroded. Therefore, it is preferable to reduce the water content as much as possible.

It is possible to obtain high-purity 1H-heptafluorocyclopentene for which the nitrogen content and the oxygen content have been reduced to 100 ppm by volume or less (preferably 50 ppm by volume or less) by performing the rectification step that purifies the crude 1H-heptafluorocyclopentene included in the crude reaction product to have a purity of 99.9 wt % or more and an organochlorine-based compound content of 350 ppm by weight or less, performing the step that removes water by bringing the resulting 1H-heptafluorocyclopentene into contact with the adsorbent, and then subjecting the resulting 1H-heptafluorocyclopentene to simple distillation. It is possible to improve dry etching stability and plasma CVD deposition stability by thus controlling the impurity content.

Therefore, the high-purity 1H-heptafluorocyclopentene according to one embodiment of the invention may suitably be used as a dry etching gas, a CVD gas, an ashing gas, and the like (plasma reaction gas). Specific examples of a preferable application of the high-purity 1H-heptafluorocyclopentene according to one embodiment of the invention include a plasma reaction dry etching gas, a plasma reaction CVD gas, and a plasma reaction ashing gas.

When using the high-purity 1H-heptafluorocyclopentene according to one embodiment of the invention, a container equipped with a valve is filled with the high-purity 1H-heptafluorocyclopentene according to one embodiment of the invention. The container may be formed of an arbitrary material as long as the container is a pressure vessel formed of a metal. The container is normally formed using manganese steel, chromium-molybdenum steel, stainless steel, nickel steel, or aluminum alloy steel. It is preferable that the valve (hereinafter may be referred to as "container valve") be a container valve that conforms to the High Pressure Gas Safety Act and HS B 8246 taking account of the corrosiveness of the compound, safety, and the like. Examples of the container valve include a diaphragm-type container valve, a key plate-type container valve, a direct diaphragm seal container valve, and the like. It is preferable to use a manganese steel container equipped with a diaphragm-type valve from the viewpoint of availability.

EXAMPLES

The invention is further described below by way of examples. Note that the scope of the invention is not limited to the following examples.

The following analysis conditions were used in the examples.

Gas Chromatography (GC)
Device: HP-6890 manufactured b Agilent Technologies
Column: Inert Cap-1 manufactured by GL Sciences Inc. (length: 60 m, inner diameter 0.25 mm, thickness: 1.5 μm)
Column temperature: held at 40° C. for 10 minutes, heated to 240° C. at 20° C./min, and held at 240° C. for 10 minutes
Injection temperature: 250° C.
Carrier gas: nitrogen
Split ratio: 100/1
Detector: FID
Analysis of Impurities (Gas Chromatography-Mass Spectrometry)
GC device: HP-6890 manufactured by Agilent Technologies
Column: Inert Cap-1 manufactured by GL Sciences Inc. (length: 60 m, inner diameter 0.25 mm, thickness: 1.5 μm)
Column temperature: held at 40° C. for 10 minutes, heated to 240° C. at 20° C./min and held at 240° C. for 10 minutes
MS device: 5973 NETWORK manufactured by Agilent Technologies
Detector: EI (accelerating voltage: 70 eV)
Measurement of Nitrogen Content and Oxygen Content (Gas Chromatography)
GC device: HP-7890 manufactured by Agilent Technologies
Column: HP-S manufactured by Agilent Technologies (length: 30 m, inner diameter 0.32 mm, thickness: 0.25 μm)
Column temperature: held at 40° C. for 5 minutes, heated to 65° C. at 5° C./min, and held at 65° C. for 1 minute
Gas sampler: 100° C.
Carrier gas: helium
Detector: TCD+pulse discharge detector
Measurement of water content (FT-IR)
IG-1000 manufactured by Otsuka Electronics Co., Ltd.
Cell length: 10 m Production Example Production of Crude 1H-heptafluorocyclopentene A SUS316 reaction tube (diameter: 1 inch, length: 1 m) was charged with 35 g of a 2% Pd-0.2% Bi catalyst (support: activated carbon, particle size: about 3 mm), and hydrogen gas was continuously fed to the reaction tube for 2 hours at a flow rate of 1500 ml/min through a mass flow controller. The reaction tube was maintained at 150° C. by circulating a heat medium. After adjusting the flow rate of the hydrogen gas to 830 ml/min, 1-chloroheptafluorocyclopentene (raw material) was fed to a vaporizer (heated at 100° C.) at a rate of 5 g/min using a pump, and then introduced into the reaction tube. Gas discharged from the reaction tube was bubbled through a potassium hydroxide aqueous solution contained in a glass flask, and a gas component discharged from the glass flask was collected into a glass trap that was cooled with dry ice/ethanol. The above reaction was continuously effected for about 2 weeks to obtain about 79 kg of crude 1H-heptafluorocyclopentene. The resulting crude 1H-heptafluorocyclopentene was analyzed by gas chromatography. It was found that the crude 1H-heptafluorocyclopentene was a mixture mainly including 1H-heptafluorocyclopentene (59.77 wt %), 1-chloroheptafluorocyclopentene (12.26 wt %), 1H,1H,2H-heptafluorocyclopentane (11.55 wt %), 1H,2H-hexafluorocyclopentene (1.33 wt %), and hexafluorocyclopentane (10.26 wt %).

Preparation of Sample 1

A still (capacity: 50 L) of a SUS316 rectifying column (number of theoretical plates: 50, packing material: Sulzer Packing) was charged with 35.7 kg of the crude H-heptafluorocyclopentene produced as described above, and heated to 100° C. Cooling water (about 10° C.) was circulated through a reflux condenser. The inside of the system was stabilized by total reflux (about 12 hours). When the temperature of the top part of the rectifying column had reached 46° C., distillation was performed while setting the reflux ratio to 40:1. 24.6 g of 1 H-heptafluorocyclopentene purified by distillation was thus obtained (yield: 70% (based on the crude 1 H-heptafluorocyclopentene)).

22 kg of the resulting 1H-heptafluorocyclopentene was put into a SUS316 tank (capacity: 20 L, electropolished inner surface). A SUS316 tube (diameter: 1 inch, length: 60 cm) was charged with a molecular sieve 3A (manufactured by Union Showa K.K.) (200 cm$^3$), and the 1H-heptafluorocyclopentene was fed from the SUS316 tank using a pinup to remove water. The 1H-heptafluorocyclopentene discharged from the outlet of the SUS316 tube was returned to the SUS316 tank, and circulated. When 8 hours had elapsed, about 100 g of the 1H-heptafluorocyclopentene contained in the SUS316 tank was sampled into a small cylinder. The water content in the sampled H-heptafluorocyclopentene (determined by FT-IR) was 9 ppm by weight.

A simple distillation apparatus was assembled by providing a short column, a condenser, and a receiver over a SUS316 still (capacity: 20 L), and cooling water (10° C.) was circulated through the condenser. 15 kg of the 1H-heptafluorocyclopentene from which water had been removed was put into the still, and the still was heated to 80° C. The nitrogen content and the oxygen content in the 1H-heptafluorocyclopentene (determined by gas chromatography) were 1418 ppm by volume and 638 ppm by volume, respectively The simple distillation operation was stopped when 30 wt % of the 1 H-heptafluorocyclopentene had been distilled into the receiver, and the still was cooled to room temperature. A manganese steel cylinder (capacity: 10 L, inner surface roughness: 1S) equipped with a diaphragm-type valve was charged with 10 kg of the 1H-heptafluorocyclopentene contained in the still. Table 1 shows the components of the 1H-heptafluorocyclopentene (sample (1)) determined by gas chromatography, as well as the measurement results for the nitrogen content, the oxygen content, and the water content.

Preparation of Samples 2 to 6

1H-Heptafluorocyclopentene (samples 2 to 6) contained in a cylinder was obtained in the same manner as described above (see "Preparation of sample 1"), except that the reflux ratio and the distillation count were changed. Table 1 shows the components of the samples 2 to 6 determined by gas chromatography, as well as the measurement results for the nitrogen content, the oxygen content, and the water content.

TABLE 1

| | Composition (wt %) | | | | | Organochlorine-based compound (ppm) | Nitrogen content (ppm by volume) | Oxygen content (ppm by volume) | Water content (ppm by weight) |
| --- | --- | --- | --- | --- | --- | --- | --- | --- | --- |
| | F7E | MCL | $C_5ClF_9$ | F8E | $C_5HF_7O$ | | | | |
| Sample 1 | 99.986154 | 0.010645 | 0.000801 | 0.001248 | 0.001152 | 114 | 41 | 33 | 14 |
| Sample 2 | 99.977029 | 0.019525 | 0.001246 | 0.001056 | 0.001144 | 208 | 50 | 38 | 12 |
| Sample 3 | 99.967507 | 0.027800 | 0.002093 | 0.001326 | 0.001274 | 299 | 44 | 36 | 16 |
| Sample 4 | 99.963415 | 0.031082 | 0.002703 | 0.001372 | 0.001428 | 338 | 55 | 35 | 15 |
| Sample 5 | 99.956751 | 0.037897 | 0.002852 | 0.001275 | 0.001225 | 407 | 51 | 41 | 12 |
| Sample 6 | 99.941344 | 0.050738 | 0.005018 | 0.001392 | 0.001508 | 558 | 49 | 39 | 14 |

F7E: 1H-heptafluorocyclopentene
MCL: 1-chloroheptafluorocyclopentene
$C_5ClF_9$: chlorononafluorocyclopentane
F8E: octafluorocyclopentene
$C_5HF_7O$: heptafluorocyclopentanone Evaluation Methods (1) Change in Purity of H-heptafluorocyclopentene (Purity Change Determination Test)

The 1H-heptafluorocyclopentene (that had been subjected to distillation purification, water removal, and simple distillation) was subjected to a purity change determination test that determines a change in purity when the 1H-heptafluorocyclopentene is continuously fed from the cylinder.

The 1H-heptafluorocyclopentene was distilled from the container at a rate of 25 sccm/min through a mass flow controller, and the purity of the 1H-heptafluorocyclopentene and the organochlorine-based compound content were determined by gas chromatography at each distillation time shown in Table 2.

(2) Evaluation of Dry Etching Using 1H-heptafluorocyclopentene

Dry etching was performed using the 1H-heptafluorocyclopentene (that had been subjected to the purity change determination test) utilizing a capacitively-coupled plasma (CCP) dry etching device.

A silicon wafer (diameter: 20 cm) (obtained by applying a photoresist (mask, 0.6 μm) to a silicon oxide film (thickness: 2 μm), and forming a hole pattern (0.1 μm)) was placed in a chamber of the etching device. After evacuating the system, argon gas, the 1H-heptafluorocyclopentene, and oxygen gas were introduced at a. flow rate of 300 sccm, 25 sccm, and 30 sccm, respectively, and dry etching was performed for 2 minutes while maintaining the pressure at 10 mTorr.

The etching rate achieved using the 1H-heptafluorocyclopentene (dry etching gas) distilled for an arbitrary distillation time was evaluated based on the etching rate achieved when the distillation time was 25 hours.

Evaluation Results

Table 2 Shows the results of the purity change determination test and the dry etching evaluation results (samples 1 to 6).

the distillation time was 750 hours (samples 1 to 4) (see the dry etching evaluation results).

When the organochlorine-based compound content was 407 ppm by weight, a decrease in etching rate was 11% or more when the distillation time was 600 hours (sample 5). When the organochlorine-based compound content was 558 ppm by weight, a decrease in etching rate was 11% or more when the distillation time was 400 hours, and etching stopped when the distillation time was 650 hours (sample 6).

The invention claimed is:

1. 1H-Heptafluorocyclopentene having a purity of 99.9 wt % or more, an organochlorine-based compound content of 338 ppm by weight or less, a nitrogen content of 100 ppm by volume or less, and an oxygen content of 50 ppm by volume or less.

2. The 1H-heptafluorocyclopentene according to claim 1, the 1H-heptafluorocyclopentene being obtained by performing a step (I) that hydrogenates 1-chloroheptafluorocyclopentene through a gas phase reaction in the presence of a catalyst to obtain crude 1H-heptafluorocyclopentene, and a step (II) that purifies the crude 1H-heptafluorocyclopentene obtained by the step (I) using a rectifying column that has a number of theoretical plates of 50 or more.

TABLE 2

| | | Sample 1 | | Sample 2 | | Sample 3 | |
|---|---|---|---|---|---|---|---|
| | Distillation time (hr) | F7E (wt %) | Organochlorine-based compound (ppm) | F7E (wt %) | Organochlorine-based compound (ppm) | F7E (wt %) | Organochlorine-based compound (ppm) |
| Purity change determination test | 0 | 99.986 | 114 | 99.977 | 208 | 99.968 | 299 |
| | 25 | 99.986 | 116 | 99.977 | 211 | 99.967 | 306 |
| | 100 | 99.985 | 122 | 99.976 | 223 | 99.965 | 327 |
| | 200 | 99.985 | 129 | 99.974 | 239 | 99.962 | 358 |
| | 400 | 99.983 | 146 | 99.970 | 275 | 99.955 | 428 |
| | 600 | 99.981 | 164 | 99.966 | 316 | 99.947 | 513 |
| | 650 | 99.981 | 169 | 99.965 | 327 | 99.944 | 537 |
| | 700 | 99.967 | 307 | 99.950 | 478 | 99.936 | 623 |
| | 750 | 99.939 | 588 | 99.929 | 689 | 99.921 | 768 |
| Dry etching evaluation (based on etching rate achieved when distillation time was 25 hours) | | Decrease in etching rate when distillation time was 750 hours was ≤10% | | Decrease in etching rate when distillation time was 750 hours was ≤10% | | Decrease in etching rate when distillation time was 750 hours was ≤10% | |

| | | Sample 4 | | Sample 5 | | Sample 6 | |
|---|---|---|---|---|---|---|---|
| | Distillation time (hr) | F7E (wt %) | Organochlorine-based compound (ppm) | F7E (wt %) | Organochlorine-based compound (ppm) | F7E (wt %) | Organochlorine-based compound (ppm) |
| Purity change determination test | 0 | 99.963 | 338 | 99.957 | 407 | 99.941 | 558 |
| | 25 | 99.963 | 345 | 99.955 | 426 | 99.938 | 586 |
| | 100 | 99.951 | 366 | 99.949 | 488 | 99.929 | 681 |
| | 200 | 99.958 | 396 | 99.939 | 584 | 99.914 | 832 |
| | 400 | 99.951 | 465 | 99.914 | 837 | 99.873 | 1241 |
| | 600 | 99.943 | 546 | 99.878 | 1200 | 99.812 | 1851 |
| | 650 | 99.940 | 568 | 99.866 | 1313 | 99.793 | 2046 |
| | 700 | 99.927 | 707 | 99.854 | 1437 | 99.771 | 2261 |
| | 750 | 99.910 | 867 | 99.840 | 1572 | 99.747 | 2499 |
| Dry etching evaluation (based on etching rate achieved when distillation time was 25 hours) | | Decrease is etching rate when distillation time was 750 hours was ≤10% | | Decrease in etching rate when distillation time was 600 hours was >10% | | Decrease in etching rate when distillation time was 400 hours was >10% Etching stopped when distillation time was 650 hours | |

As shown in Table 2, an organochlorine-based compound (1-chloroheptafluorocyclopentene and chlorononafluorocyclopentane) having a boiling point higher than that of 1H-heptafluorocyclopentene was concentrated as the distillation time from the container increased (see the results of the purity change determination test). When the organochlorine-based compound content was 350 ppm by weight or less, a decrease in etching rate was 10% or less even when 3. The 1H-heptafluorocyclopentene according to claim 1, wherein the organochlorine-based compound is either or both of chlorononafluorocyclopentane and chloroheptafluorocyclopentene.

4. The 1H-heptafluorocyclopentene according to claim 3, the 1H-heptafluorocyclopentene having a water content of 20 ppm by weight or less.

5. A method for using the 1H-heptafluorocyclopentene according to claim 1 as a dry etching gas.

6. A method for using the 1H-heptafluorocyclopentene according to claim 1 as a plasma CVD reactive gas.

7. A container equipped with a valve that is filled with the 1H-heptafluorocyclopentene according to claim 4.

* * * * *